US011224399B2

(12) United States Patent
Lee et al.

(10) Patent No.: US 11,224,399 B2
(45) Date of Patent: Jan. 18, 2022

(54) APPARATUS AND METHOD USING DEEP LEARNING (DL) TO COMPENSATE FOR LARGE FOCAL SPOT SIZE IN X-RAY PROJECTION IMAGING

(71) Applicant: CANON MEDICAL SYSTEMS CORPORATION, Otawara (JP)

(72) Inventors: Tzu-Cheng Lee, Vernon Hills, IL (US); Jian Zhou, Vernon Hills, IL (US); Zhou Yu, Vernon Hills, IL (US)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 82 days.

(21) Appl. No.: 16/510,594

(22) Filed: Jul. 12, 2019

(65) Prior Publication Data

US 2021/0007702 A1 Jan. 14, 2021

(51) Int. Cl.

| | |
|---|---|
| ***G06T 7/00*** | (2017.01) |
| ***A61B 6/00*** | (2006.01) |
| ***G06N 3/08*** | (2006.01) |
| *A61B 6/03* | (2006.01) |
| *G06N 3/04* | (2006.01) |
| *G06N 20/00* | (2019.01) |

(Continued)

(52) U.S. Cl.

CPC ............. *A61B 6/584* (2013.01); *G06N 3/084* (2013.01); *G06T 7/0012* (2013.01); *A61B 6/032* (2013.01);

(Continued)

(58) Field of Classification Search

CPC ......... G06T 7/0012; G06T 2207/10148; G06T 2207/20081; G06T 2207/10081;

(Continued)

(56) References Cited

U.S. PATENT DOCUMENTS

| | | | |
|---|---|---|---|
| 9,389,172 B2 * | 7/2016 | Federici | ............. G01N 21/3586 |
| 2018/0018757 A1 | 1/2018 | Suzuki | |
| 2019/0030371 A1 | 1/2019 | Han | |

FOREIGN PATENT DOCUMENTS

| | | |
|---|---|---|
| CN | 107644225 A * | 1/2018 |
| EP | 3 447 731 A1 | 8/2017 |
| WO | WO 2017/223560 A1 | 12/2017 |

OTHER PUBLICATIONS

Gjesteby et al., Deep learning methods to guide CT image reconstruction and reduce metal artifacts, Feb. 11-16, 2017 [retrieved Jan. 28, 2021], SPIE Medical Imaging: Medical Imaging 2017: Physics of Medical Imaging, Proceedings vol. 10132, 8 pages. Retrieved: https://doi.org/10.1117/12.2254091 (Year: 2017).*

(Continued)

*Primary Examiner* — Matthew C Bella
*Assistant Examiner* — Dennis Rosario
(74) *Attorney, Agent, or Firm* — Oblon, McClelland, Maier & Neustadt, L.L.P.

(57) ABSTRACT

A method and apparatus is provided that uses a deep learning (DL) network to correct projection images acquired using an X-ray source with a large focal spot size. The DL network is trained using a training dataset that includes input data and target data. The input data includes large-focal-spot-size X-ray projection data, and the output data includes small-focal-spot-size X-ray projection data (i.e., smaller than the focal spot of the input data). Thus, the DL network is trained to improve the resolution of projection data acquired using a large focal spot size, and obtain a resolution similar to what is achieved using a small focal spot size. Further, the DL network is can be trained to additional correct other aspects of the projection data (e.g., denoising the projection data).

20 Claims, 8 Drawing Sheets

(51) Int. Cl.
*G16H 30/40* (2018.01)
*G16H 50/20* (2018.01)

(52) U.S. Cl.
CPC ............... *G06N 3/04* (2013.01); *G06N 20/00* (2019.01); *G06T 2207/10081* (2013.01); *G06T 2207/20081* (2013.01); *G06T 2207/20084* (2013.01); *G16H 30/40* (2018.01); *G16H 50/20* (2018.01)

(58) Field of Classification Search
CPC ....... G06T 2207/20084; G06T 2210/41; G06T 2207/10116; G06T 2207/30004; G06T 2207/30068; G06T 2207/30008; G06T 11/006; G06T 5/003; G06T 3/4046; G06T 2207/10072; G06T 2211/421; A61B 6/032; A61B 5/7267; A61B 5/0075; A61B 5/055; G06N 20/00; G06N 3/04; G06N 3/08; G06K 2209/05; H04N 5/23212
See application file for complete search history.

(56) References Cited

OTHER PUBLICATIONS

Machine translation of said CN 107644225 A to Xue Xingying, retrieved Jun. 30, 2021, 9 pages. Retrieved: https://patents.google.com/patent/CN107644225A/en?oq=cn 107644225 (Year: 2021).*

Peng et al., Focal Spot Intensity Distribution Estimation of X-ray tube via Machine Learning, Jul. 2-4, 2019 [retrieved Jun. 30, 2021], International Symposium on Digital Industrial Radiology and Computed Tomography, 8 pages. Retrieved: https://www.ndt.net/search/docs.php3?id=24742 (Year: 2019).*

Gjesteby, Lars et al, Deep learning methods to guide CT image reconstruction and reduce metal artifacts, https://www.spiedigitallibrary.org/conference-proceedings-of-spie/10132/101322W/Deep-learning-methods-to-guide-CT-image-reconstruction-and-reduce/10.1117/12.2254091.short?SSO=1, Mar. 9, 2017.

Yang, C-Y. et. al, "Single-image super-resolution: A benchmark" *European Conference on Computer Vision* 2014; 372-386.

Dong, C. et. al, "Super-Resolution Using Deep Convolutional Networks" arXic.org 2015: 1501:00092v3.

Ledig, C. et. al, "Photo-Realistic Single Image Super-Resolution Using a Generative Adversarial Network" arXic.org 2016: 1209:04802v5.

Umehara, K. et. al, 'Application of Super-Resolution Convolutional Neural Network for Enhancing Image Resolution in Chest CT,' *J Digit Imaging* 2018; 31(4): 441-450.

Yu, H. et. al,"Computed tomography super-resolution using convolutional neural networks," *2017 IEEE International Conference on Image Processing* (*ICIP*) 2017.

Extended European Search Report dated Nov. 16, 2020 in European Patent Appiication No. 20184932.0, 8 pages.

Jan Kuntz, et al., "Focal Spot Deconvolution using Convolutional Neural Networks", Medical Imaging 2019: Physics of Medical Imaging, XP055746391, Mar. 2019, 6 pages.

* cited by examiner 500
501
508
SLIP RING
507
ROTATING UNIT
S
RA
502
X-RAY DETECTOR
503
DATA ACQUISITION CIRCUIT (DAS)
504
NONCONTACT DATA TRANSMITTER
505
506
CURRENT REGULATOR
513
HIGH VOLTAGE GENERATOR
509
SYSTEM CONTROLLER
510
514
RECONSTRUCTION DEVICE
511
512
STORAGE DEVICE
516
DISPLAY DEVICE
515
INPUT DEVICE
PREPROCESSING DEVICE

APPARATUS AND METHOD USING DEEP LEARNING (DL) TO COMPENSATE FOR LARGE FOCAL SPOT SIZE IN X-RAY PROJECTION IMAGING

FIELD

This disclosure relates to using a deep learning (DL) neural network to minimize the degradation of resolution resulting from acquiring X-ray projection data using of a large focal spot size in the X-ray tube.

BACKGROUND

The background description provided herein is for the purpose of generally presenting the context of the disclosure. Work of the presently named inventors, to the extent the work is described in this background section, as well as aspects of the description that cannot otherwise qualify as prior art at the time of filing, are neither expressly nor impliedly admitted as prior art against the present disclosure.

Radiography systems and methods are widely used, particularly for medical imaging and diagnosis. Radiography systems generally create two-dimensional projection images through a subject's body. A radiation source, such as an X-ray tube, irradiates the body from one side. A collimator, generally adjacent to the X-ray source, limits the angular extent of the X-ray beam, so that radiation impinging on the body is substantially confined to a cone-beam/fan-beam region (i.e., an X-ray projection volume) defining an image volume of the body. At least one detector on the opposite side of the body receives radiation transmitted through the body substantially in the projection volume. The attenuation of the radiation that has passed through the body is measured by processing electrical signals received from the detector.

X-ray projection images having high spatial resolution are desirable in order to visualize fine details in the image. However, spatial resolution can be limited by the detector pixel size. Additionally, the spatial resolution can be limited by the spatial extent of the X-ray source (i.e., the focal spot size), and the geometrical arrangement among the source, the imaged object, and the X-ray detector. The short wavelength of X-rays minimizes the effects of diffraction. However, as the size and spacing of the pixels of the X-ray detector array continue to get smaller with improvements in detector technology, improvements to decreasing the size of the focal-spot size in X-ray sources have failed to keep pace, resulting in the X-ray source being the limiting factor in resolution. Due to intrinsic material and thermal constraints in X-ray tubes, the focal spot size has remained relatively constant, whereas the critical dimensions of the X-ray detector array (e.g. the width and spacing of the detector elements in the array) have decreased over time, until now the spatial resolution for X-ray detects is smaller than the width of the point-spread function of X-ray sources operating under typical clinical settings.

The focal spot is the point where the electron beam strikes a target within an X-ray tube. Thus, the focal-spot size is determined by the size of the electron beam and the aspect angle between the surface struck by the X-rays and the direction from the X-ray source to the target. A small focal-spot size improves the resolution of the X-ray imaging, resulting in more detailed images. However, it is often difficult to use a small focal-spot size due to the constraints imposed by X-ray tube loading necessary to achieve a desired exposure and signal-to-noise-ratio (SNR).

The width of the focal spot is not the only factor determining the point-spread function. Additionally, the point-spread function is affected by the ratio between object-imager distance (OID) and source-imager distance (SID). The closer an object is to the detector and the farther away the object is from the source, the smaller the point-spread function becomes, resulting in less blurring in the generated image. Thus, the spatial resolution can be improved by making the ratio SID:OID large. This can be accomplished by keeping the OID to a minimum, e.g., by keeping the object close to the detector. Further, the ratio SID:OID is large when the SID is large by positioning the object a long distance from the X-ray source. However, practical constraints impose bounds on how large the ratio SID:OID can be for clinical applications.

In clinical X-ray imaging systems, the focal-spot size is typically on the order of one millimeter, which is large enough to be the limiting factor for the X-ray image resolution. High-resolution detectors with a pixel size significantly less than one millimeter create potential for higher resolution X-ray imaging, but this potential cannot be fully realized without overcoming the practical limitations imposed by the size of focal spots and magnification factors. Tube design limitations present obstacles to improve X-ray imaging resolution without degrading the SNR by decreasing the exposure. A method of increasing resolution without significantly degrading SNR in X-ray images would be advantageous.

This resolution limit arising for the spot-size not only affects fluoroscopy, but also impacts other modalities of X-ray radiography, such as X-ray computed tomography (CT). X-ray CT systems and methods are widely used, particularly for medical imaging and diagnosis. CT systems generally create images of one or more sectional slices through a subject's body. A radiation source, such as an X-ray source, irradiates the body from one side. At least one detector on the opposite side of the body receives radiation transmitted through the body. The attenuation of the radiation that has passed through the body is measured by processing electrical signals received from the detector.

A CT sinogram indicates attenuation through the body as a function of position along a detector array and as a function of the projection angle between the X-ray source and the detector array for various projection measurements. In a sinogram, the spatial dimensions refer to the position along the array of X-ray detectors. The time/angle dimension refers to the projection angle of X-rays, which changes as a function of time during a CT scan. The attenuation resulting from a portion of the imaged object (e.g., a vertebra) will trace out a sine wave around the vertical axis. Those portions farther from the axis of rotation correspond to sine waves with larger amplitudes, and the phase of the sine waves corresponds to the angular positions of objects around the rotation axis. Performing an inverse Radon transform—or any other image reconstruction method—reconstructs an image from the projection data in the sinogram.

Factors that limit the spatial resolution of the sinogram will also limit the resolution of the reconstructed image. Accordingly, improved resolution methods in the projection domain can provide a benefit for many areas of X-ray radiography.

The "background" description provided herein is for the purpose of generally presenting the context of the disclosure. Work of the presently named inventors, to the extent it is described in this background section, as well as aspects of the description which may not otherwise qualify as conventional art at the time of filing, are neither expressly nor implicitly admitted as conventional art against the present disclosure.

BRIEF DESCRIPTION OF THE DRAWINGS

A more complete understanding of the disclosure is provided by reference to the following detailed description when considered in connection with the accompanying drawings, wherein.

DETAILED DESCRIPTION

Practical constraints limit the smallest focal-spot size for X-ray tubes used as X-ray sources for projective imaging, and this limit to the focal-spot size in turn limits the resolution achievable in such applications as radiography, computed tomography, fluoroscopy, and angiography. These constraints include practical size limitations, heat transfer and material characteristics, dose constraints (e.g., maintaining the radiation dosage as low as reasonably possible), and time constraints. As a practical matter, a larger focal-spot size can generate a greater flux of X-rays resulting in a higher signal-to-noise ratio (SNR) in the projection images, but the larger focal-spot size comes at the cost a poorer spatial resolution. The methods and apparatus described herein combine the best of large and small focal-spot sizes by acquiring a training dataset including projection images using both a large and a small focal-spot sizes, and then training a neural network to achieve the image resolution of a small focal-spot size from projection images acquired using a large focal-spot size without sacrificing the high SNR achieved with the large focal-spot size. Thus, the methods described herein can generate projection images that have both good spatial resolution similar to an image generated using a small focal-spot size and the larger SNR of an image generated using a large focal-spot size. The importance of achieving good spatial resolution is becoming more significant as X-ray detector sizes continue to decrease.

Figure 1A:
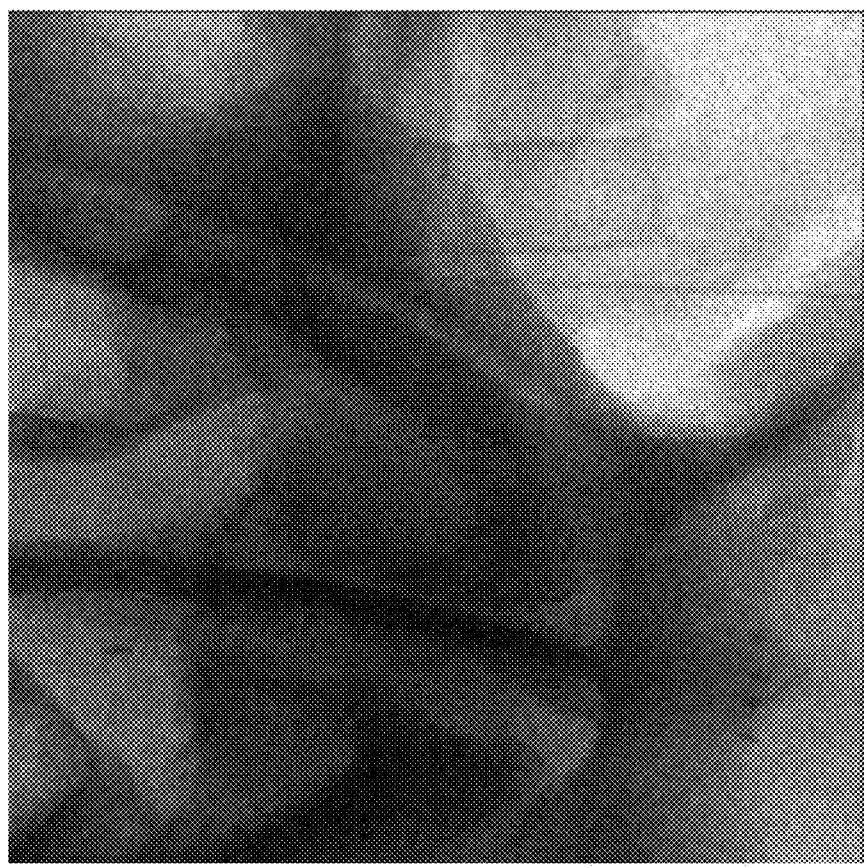
FIG. 1A is a projection image generated using a small focal spot and a relatively small X-ray exposure, according to one implementation.
Figure 1B:
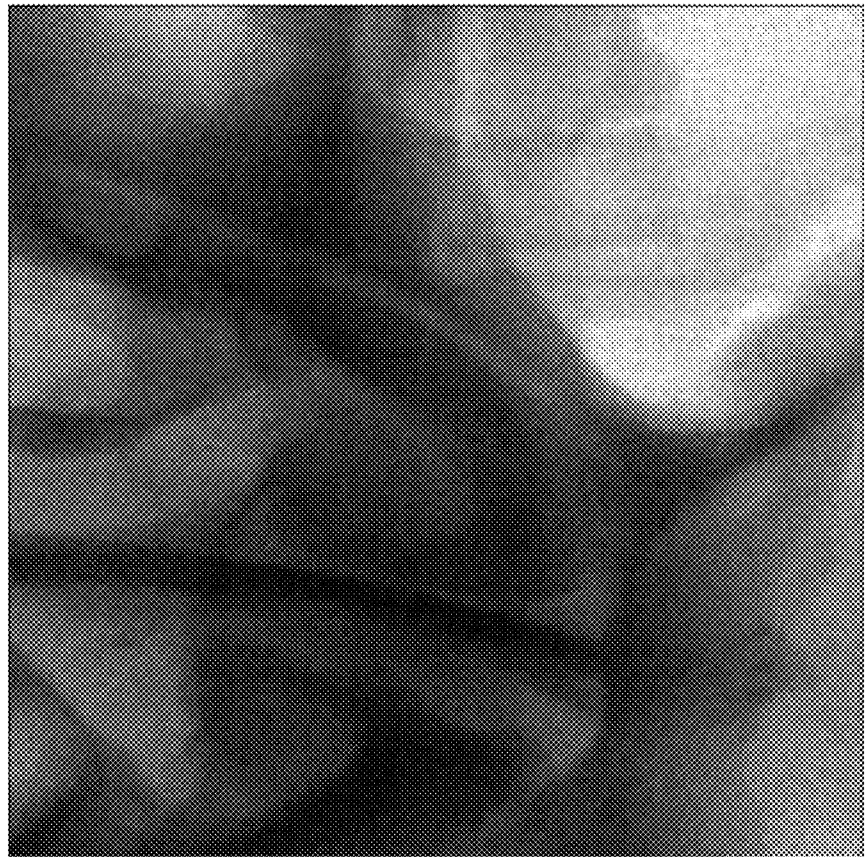
FIG. 1B is a projection image generated using a focal spot that is larger than the focal spot used to obtain FIG. 1A and the exposure is twice as large as in FIG. 1A, according to one implementation.

Referring now to the drawings, wherein like reference numerals designate identical or corresponding parts throughout the several views, FIGS. 1A and 1B show two projection images taken using different focal-spot sizes. FIG. 1A shows an X-ray projection image acquired using a smaller focal-spot size than the focal-spot size used to acquire the X-ray projection image shown in FIG. 1B. The focal spot in FIG. 1A is smaller than in FIG. 1B, and the X-ray exposure from FIG. 1B is twice as larger as in FIG. 1A. Higher resolution is visible in FIG. 1A than in FIG. 1B, but FIG. 1A sacrifices SNR in order to obtain this improved resolution. This is because the X-ray flux achievable using the smaller focal-spot size is less, resulting in smaller signals and thus lower SNRs in FIG. 1A compared to FIG. 1B.

Thus, it can be observed that focal-spot sizes, such as those used for the existing clinical systems, which are significantly large relative to the critical detector dimension adversely impact the overall system resolution. While the focal-spot size depends on particular design choices and trade-offs for a given X-ray imager, generally, the focal spot for all X-ray imagers is on the order of one millimeter due to the tube loading capacity for smaller focal spots. Ideally, the focal-spot size would be made arbitrarily small, but that cannot be achieved due to X-ray tube design limitations. Ultimately, there is a trade-off between resolution and image quality. On the one hand, a larger focal-spot size can provide more exposure and greater SNR, but this greater SNR comes at the expense of poorer spatial resolution. On the other hand, smaller focal-spot sizes improve spatial resolution, but this improvement comes at the expense of less exposure and a smaller SNR.

Figure 2:
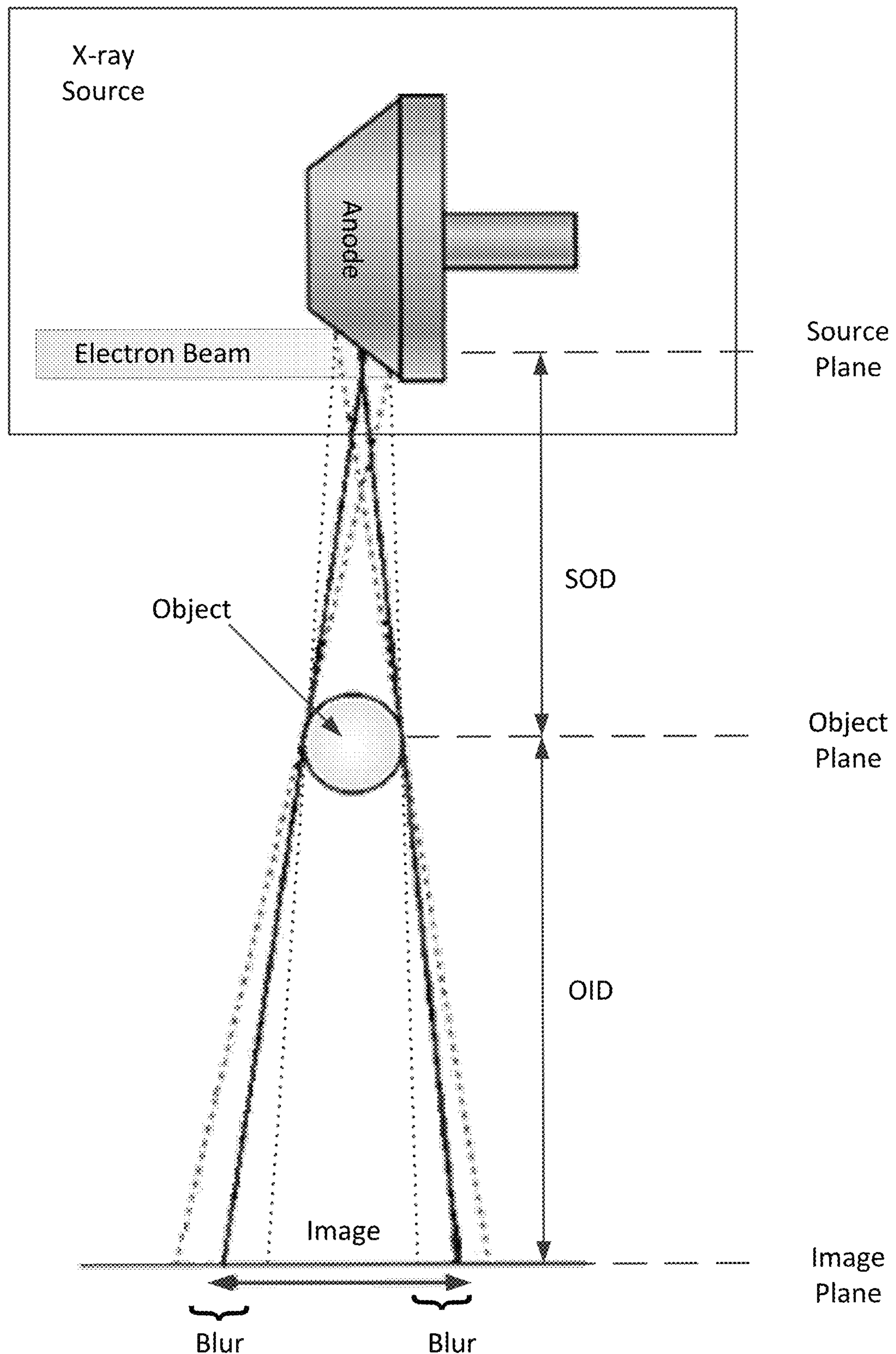
FIG. 2 shows a diagram of blurring in an X-ray projection image resulting from a finite width of a focal spot in the X-ray source, according to one implementation.

FIG. 2 illustrates an exemplary imaging system in which an object is imaged by X-rays from an X-ray source passing through the object being detected at an image plane. The size of the electron beam on the anode of the X-ray source determines the focal-spot size. The solid lines show the ray trajectories from a center of the focal spot and passing through the periphery of the object. The dashed lines show the X-ray trajectories for X-rays from the edges of the focal spot passing through the periphery of the object. When the source-to-object distance (SOD) is much greater than the object-to-imaged distance (OID), the magnification is small and the point-spread function in the image plane is reduced. The magnification and the point-spread function of the image at the image plane can also be affected by the use an X-ray filter/lens (e.g., a butterfly filter) at the source. The relationship between the geometry of the X-ray apparatus and the focal-spot size to the image resolution and point-spread function are generally well understood and can be modeled using straightforward ray tracing, and, therefore, these details are not discussed herein.

Figure 3A:
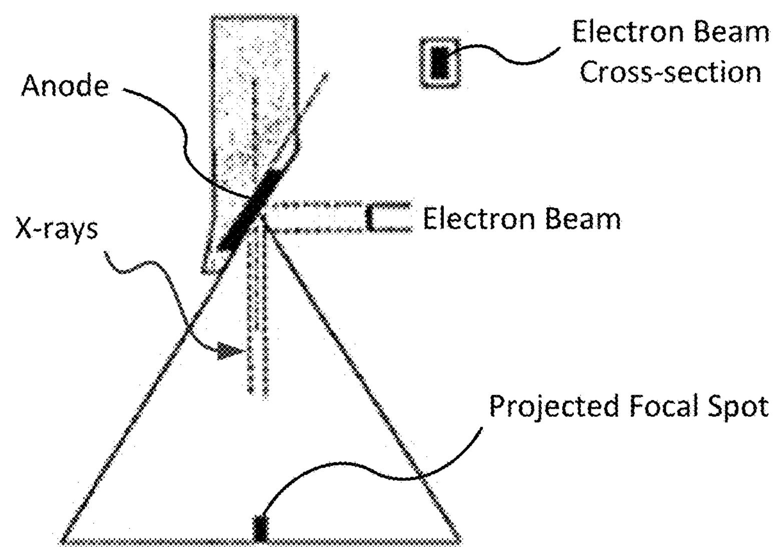
FIG. 3A shows tradeoffs for a small electron beam area combined with a large anode angle, according to one implementation.
Figure 3B:
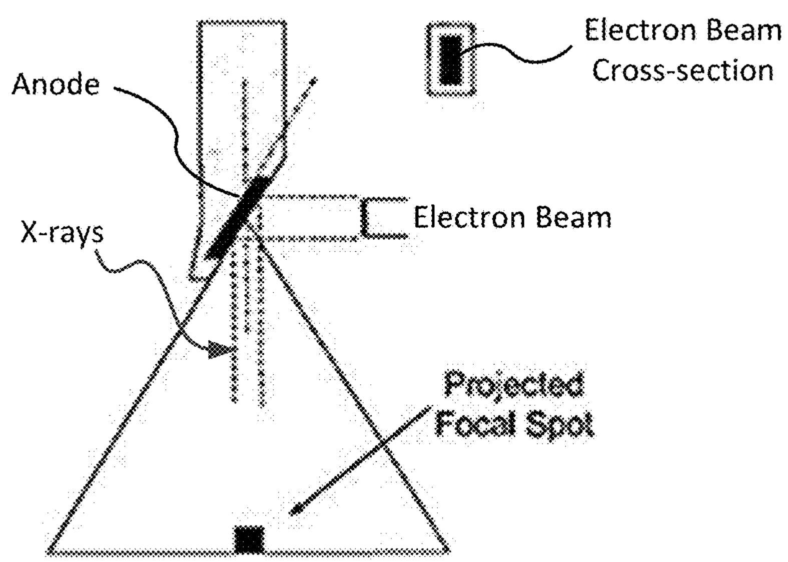
FIG. 3B shows tradeoffs for a large electron beam area combined with a large anode angle, according to one implementation.
Figure 3C:
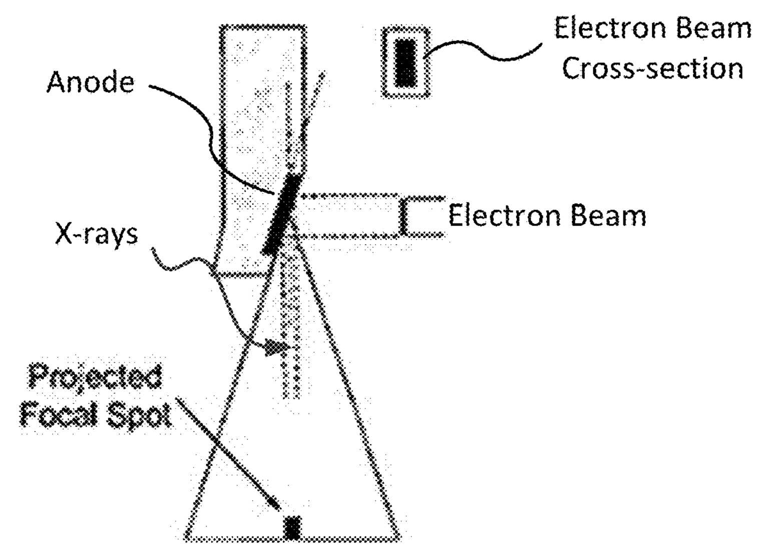
FIG. 3C shows tradeoffs for a large electron beam area combined with a small anode angle, according to one implementation.

FIGS. 3A, 3B and 3C illustrate the tradeoffs between making the electron beam and/or the anode angle bigger or smaller. In FIG. 3A, the anode angle is large and the area of the electron beam is small, resulting in good field coverage (i.e., the field of view is large due to the large beam angle), small focal spot size for good resolution, but poor power loading (i.e., the X-ray flux is low resulting in either low SNR or long exposure time at a given view angle to compensate for the low flux rate). In FIG. 3B, the anode angle is large and the area of the electron beam is large, resulting in good field coverage, large focal spot size for poorer resolution, and good power loading. In FIG. 3C, the anode angle is small and the area of the electron beam is large, resulting in narrower/poor field coverage, small focal spot size for good resolution, and good power loading. These tradeoffs also impact other aspects of CT imaging, such as manufacturing costs and limitations of the size of patients. For examples, using a smaller effective focal spot size, results in lower power loading or smaller filed coverage, and, in turn, these factors limit the practicability of applying the finer focal size (e.g., 0.4×0.5 mm) to larger and more strongly attenuating patients (e.g., larger patients can require a larger beam angles and a higher mA setting, such as 500 mA). Further, large power loading smaller effective focal spot size can increase the manufacturing costs.

Figure 4:
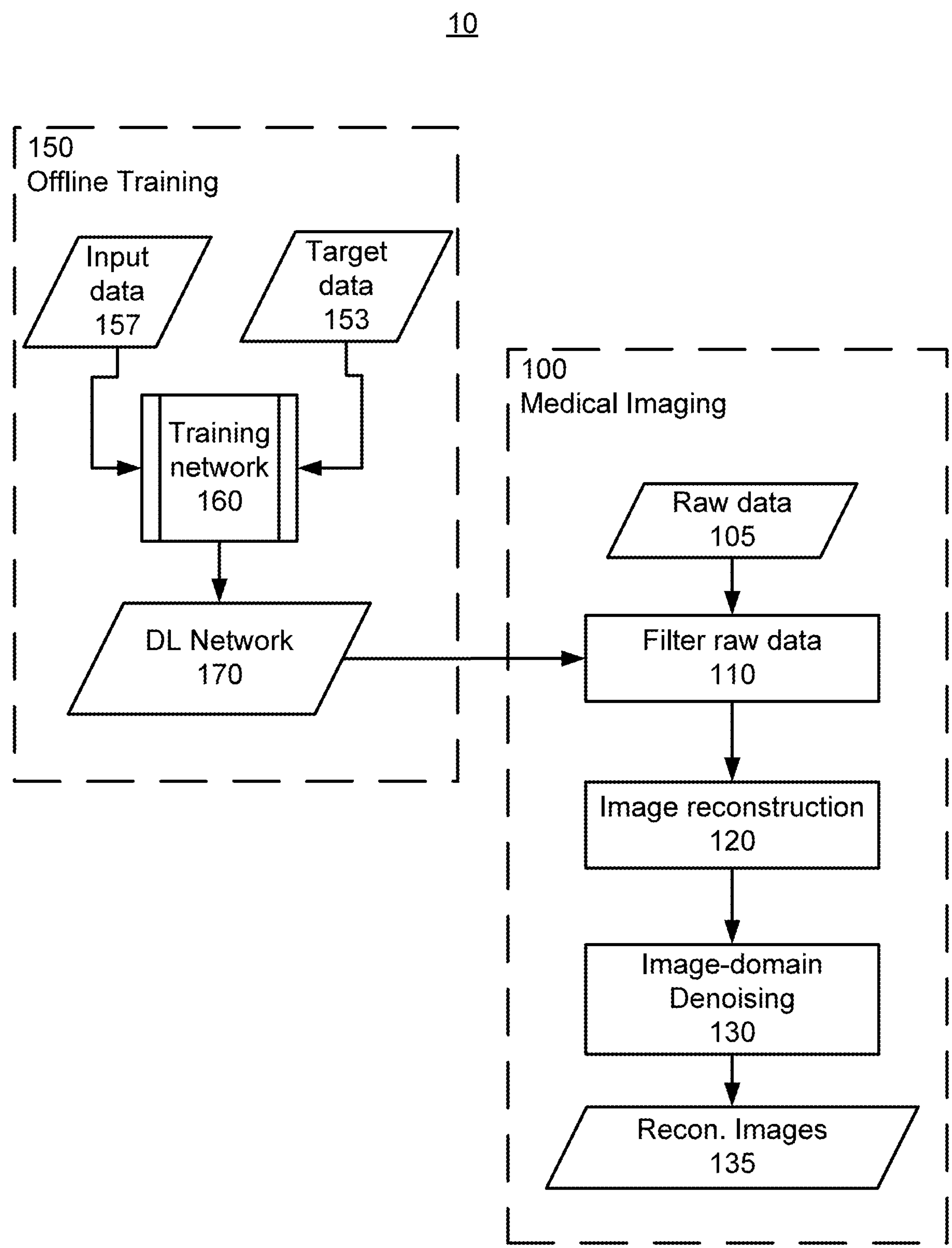
FIG. 4 shows a flow diagram of a method of training a deep learning (DL) network and then using the DL network to correct the projection data and then perform reconstruction, according to one implementation.

FIG. 4 shows a flow diagram for a non-limiting example of a method 10 that trains and uses a DL neural network 170 to perform data-domain corrections to X-ray projection data (e.g., edge/resolution enhancement, sinogram restoration, denoising, and/or artifact correction). Method 10, as illustrated in FIG. 4, uses the DL network 170 to learn how to optimal filter raw data 105 (e.g., a sinogram), and then reconstructs a CT image from the Filtered data. Method 10 includes two parts: (i) an offline training process 150 and (ii) a medical imaging process 100. That is, process 150 trains the DL network 170, and process 100 uses the trained DL network 170 to filter the raw data 105 in the projection domain, thereby generating high-quality images 135 with reduced noise and artifacts. In certain implementations such as fluoroscopy, steps 120 and 130 can be omitted and the output can be the corrected projection data.

In certain implementations, the network 170 includes a convolutional neural network (CNN) in which series of convolution, batch normalization, and rectified linear unit network layers are performed.

The network 170 is trained using process 160. In process 160, a loss function is used to iteratively adjust/optimize parameters of the DL network 170 (e.g., the parameters of the DL network 170 can include weighting coefficients connecting network layers, and activation functions/potentials of nodes within the layers). The optimization of the network parameters continues until stopping criteria are satisfied (e.g., a stopping criterion can be whether the value of the loss function converged to a predefined threshold) to generate the trained network 170.

The loss function compares target data 153 to an output generated by applying the input data 157 to a current version of the DL network 170. For example, the input data can include projection data acquired using a large focal spot size, and the target data can include projection data acquired using a small focal spot size and a large amount of averaging to reduce noise.

For a given CT scan, each low-quality (e.g., large focal spot size) sinogram of the input data forms a pair with the corresponding high-quality (e.g., small focal spot size) sinogram. The scans to acquire the low-quality sinograms for the input data 157 and the high-quality sinograms for the target data 153 can be performed on a phantom, for example.

Applying a low-quality sinogram from the input data to the current version of the DL network 170 generates an output from the network that is supposed to be a resolution-enhanced version of the low-quality sinogram (i.e., a filtered sinogram). The DL network 170 is trained by iteratively adjusting the network coefficients in the DL network 170 to minimize the difference between the Filtered sinogram output from the network 170 and the high-quality sinogram from the target data 153. The training of the network 170 is determined to be complete when the difference is minimized between the target data and the output from the DL network 170. The question of whether or not this difference has been sufficiently minimized is resolved based on one or more predetermined stopping criteria of process 160. Once the stopping criteria have been satisfied, the trained network 170 can then be stored and then later recalled to be used in the medical imaging process 100.

In alternative implementations, the DL network 170 is implemented as a residual network (ResNet). In this case, the method described herein can filter an image by treating the difference between the small and large spot size sinograms as an additive residue that can be directly removed from the low-quality sinogram. This additive residue or difference image can be thought of as a high-pass filtered version of the small-spot-size projection data. Thus, when a low-quality sinogram is applied to the neural network, the network outputs an image corresponding to the difference image. Then the corrected sinogram can be generated by subtracting the network output (the noise/artifact) from the low-quality sinogram to generate the corrected sinogram.

In method 10, a loss function is used to iteratively adjust network coefficients (e.g., weights and biases of convolutional and pooling layers) of the DL network 170 until stopping criteria are satisfied (e.g., convergence of the parameters to a predefined threshold) to generate the trained network 170. The loss function compares high-quality data 153 to results of a current version of the DL network 170 to which input data 157 is applied.

Process 100 is performed by obtaining raw data 105, e.g., by performing a CT scan to generate CT projections at a series of view angles (i.e., a low-quality sinogram). For example, the sinogram can be performed using a low-dose CT scan to generate the raw data 105.

In step 110 of process 100, the raw data 105 is filtered by applying the raw data 105 to the trained DL network 170. The DL network 170 then outputs a Filtered sinogram. In certain implementations, the DL network 170 is a convolution neural network (CNN). The CNN can be a network that directly generates local small sized filters, e.g., $$y_i = \sum_{j \in Neighbor\ of\ i} w_{ij} x_j$$

wherein $w_{ij}$ is the filter on the ith pixel.

In the training process 160, the same process as used in step 110 to generate the filtered sinograms from the raw data 105 is also used to generate output sinograms from the input data, and then compare, using the loss function, the output sinograms to the target data.

In step 120 of process 100, a CT image is reconstructed from the denoised sinogram. Various methods can be used to reconstruct CT images from projection data, including filtered back-projection (FBP) and statistical iterative reconstruction (IR) algorithms. In addition to FBP, other analytical methods can be used such as the Feldkamp Davis Kress (FDK) method Adaptive Iterative Dose Reduction 3D (AIDR 3D) method. Compared to FBP reconstruction methods, IR methods can provide improved image quality at reduced radiation doses.

One IR method performs unconstrained (or constrained) optimization to find the argument p that minimizes the expression $$\underset{p}{\operatorname{argmin}}\{\|Ap-\ell\|_W^2+\beta U(p)\},$$

wherein $\ell$ is the projection data representing the logarithm of the X-ray intensity of projection images taken at a series of projection angles and p is a reconstructed image of the X-ray attenuation for voxels/volume pixels (or two-dimensional pixels in a two-dimensional reconstructed image) in an image space. For the system matrix A, each matrix value $a_{ij}$ (i being a row index and j being a column index) represents an overlap between the volume corresponding to voxel $p_j$ and the X-ray trajectories corresponding to projection value $\ell_i$. The data-fidelity term $\|Ap-\ell\|_W^2$ is minimized when the forward projection A of the reconstructed image p provides a good approximation to all measured projection images $\ell$. Thus, the data fidelity term is directed to solving the system matrix equation $Ap=\ell$, which expresses the Radon transform (i.e., projections) of various rays from a source through an object OBJ in the space represented by p to X-ray detectors generating the values of $\ell$ (e.g., X-ray projections through the three-dimensional object OBJ onto a two-dimensional projection image $\ell$).

The notation $\|g\|_W^2$ signifies a weighted inner product of the form $g^TWg$, wherein W is the weight matrix (e.g., expressing a reliability of trustworthiness of the projection data based on a pixel-by-pixel signal-to-noise ratio). In other implementations, the weight matrix W can be replaced by an identity matrix. When the weight matrix W is used in the data fidelity term, the above IR method is referred to as a penalized weighted least squares (PLWS) approach.

The function U(p) is a regularization term, and this term is directed at imposing one or more constraints (e.g., a total variation (TV) minimization constraint) which often have the effect of smoothing or denoising the reconstructed image. The value β is a regularization parameter is a value that weights the relative contributions of the data fidelity term and the regularization term.

In step 130 of process 100, additional image-domain denoising is performed. This step is optional, and can be omitted in some implementations.

Example denoising methods include linear smoothing filters, anisotropic diffusion, non-local means, or nonlinear filters. Linear smoothing filters remove noise by convolving the original image with a convolution kern& that represents a low-pass filter or smoothing operation. For example, a Gaussian convolution kernel comprises elements determined by a Gaussian function. This convolution brings the value of each pixel into closer agreement with the values of its neighbors. Anisotropic diffusion removes noise while preserving sharp edges by evolving an image under a smoothing partial differential equation similar to the heat equation. A median filter is an example of a nonlinear filter and, if properly designed, a nonlinear filter can also preserve edges and avoid blurring. The median filter is one example of a rank-conditioned rank-selection (RCRS) filter, which can be applied to remove salt and pepper noise from an image without introducing significant blurring artifacts. Additionally, a filter using a total-variation (TV) minimization regularization term can be applied if imaged region supports an assumption of uniformity over large areas that are demarked by sharp boundaries between the uniform areas. A TV filter is another example of a nonlinear filter. Moreover, non-local means filtering is an exemplary method of determining denoised pixels using a weighted average over similar patches within the images.

Finally, a reconstructed image 135 is output having good image quality, and the reconstructed image 135 can be displayed to a user or stored for later use.

Now a more detailed description of training a DL network is provided (e.g., process 160). Here, the target data 153 are high-quality sinograms acquired using a small focal spot size in the X-ray tube, and the input data 157 are low-quality sinograms acquired using a large focal spot size, as described above.

Figure 5:
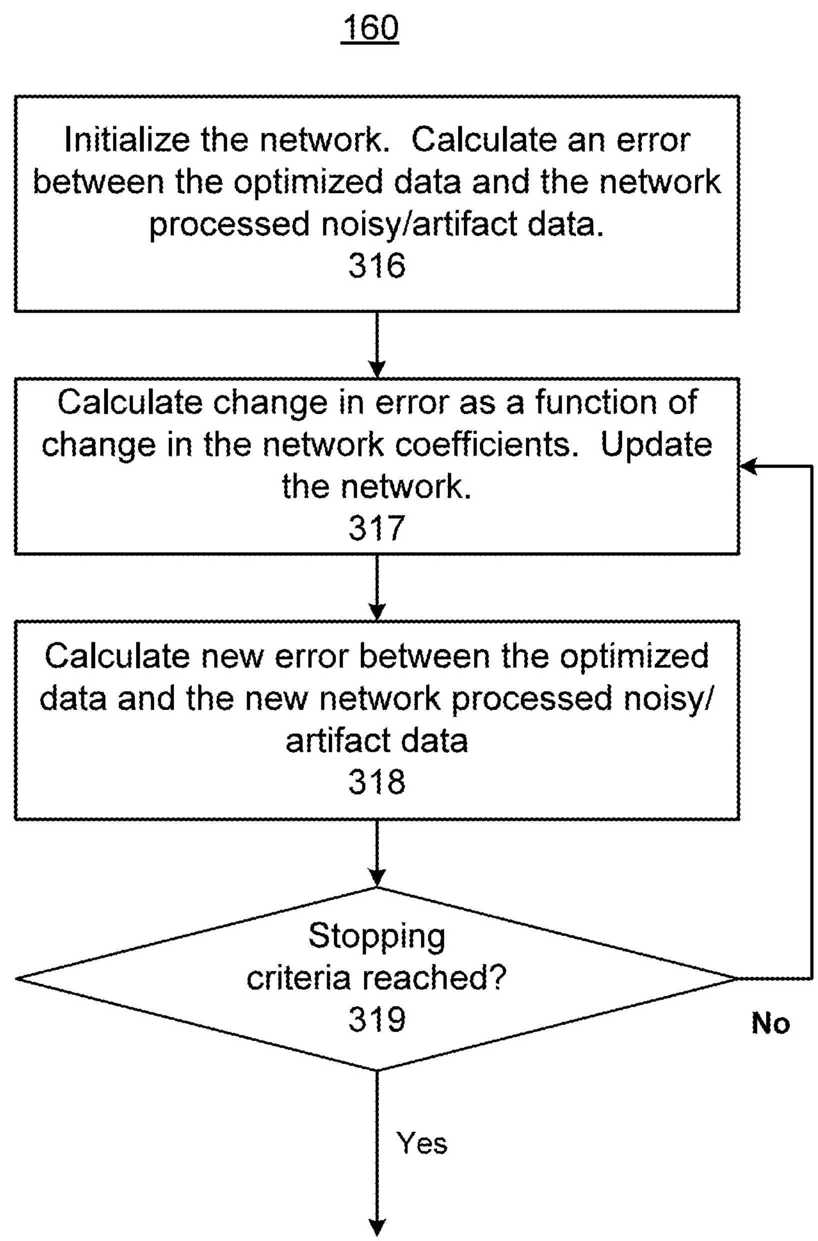
FIG. 5 shows a flow diagram of the process to train the DL network by iteratively adjusting coefficients of the DL network to optimize a loss-error function, according to one implementation.

FIG. 5 shows a flow diagram of one implementation of the training process 160. In process 160, input data 157 and target data 153 are used as training data to train a DL network 170, resulting in the DL network 170 being output from step 319 of process 160. The offline DL training process 160 trains the DL network 170 using a large number of input sinograms 157 that are paired with corresponding target sinograms 153 to train the DL network 170 to produce, from the input sinograms 157, filtered sinograms resembling the target sinograms 153.

In process 160, a set of training data is obtained, and the network 170 is iteratively updated to reduce the error (e.g., the value produced by a loss function). The DL network infers the mapping implied by the training data, and the cost function produces an error value related to the mismatch between the target sinograms 153 and the result produced by applying a current incarnation of the DL network 170 to the input sinograms 157. For example, in certain implementations, the cost function can use the mean-squared error to minimize the average squared error. In the case of a of multilayer perceptrons (MLP) neural network, the backpropagation algorithm can be used for training the network by minimizing the mean-squared-error-based cost function using a (stochastic) gradient descent method.

In step 316 of process 160, an initial guess is generated for the coefficients of the DL network 170. For example, the initial guess can be based on a priori knowledge of the region being imaged or one or more exemplary denoising methods, edge-detection methods, and/or blob detection methods. Additionally, the initial guess can be based on one of a LeCun initialization, an Xavier initialization, and a Kaiming initialization.

Steps 316 through 319 of process 160 provide a non-limiting example of an optimization method for training the DL network 170.

An error is calculated (e.g., using a loss function or a cost function) to represent a measure of the difference (e.g., a distance measure) between the target sinograms 153 (i.e., ground truth) and input sinograms 157 after applying a current version of the network 170. The error can be calculated using any known cost function or distance measure between the image data, including those cost functions described above. Further, in certain implementations the error/loss function can be calculated using one or more of a hinge loss and a cross-entropy loss. In certain implementations, the loss function can be the $\ell_p$-norm of the difference between the target data and the result of applying the input data to the DL network 170. Different values of "p" in the $\ell_p$-norm can be used to emphasize different aspects of the noise. Further, a weighting mask (e.g., based on the attenuation coefficient of signal intensity) can be applied on a pixel-by-pixel basis to the difference between the target data and the result generated from the input data. In certain implementations, rather than minimizing an $\ell_p$-norm of the difference between the target data and the result from the input data, the loss function can represent a similarity (e.g., using a peak signal-to-noise ratio (PSNR) or a structural similarity (SSIM) index).

In certain implementations, the training is performed by minimizing the following loss function $$\hat{\theta} = \underset{\theta}{\operatorname{argmin}} \frac{1}{N} \sum_{n} L(\bar{y}^{(n)}, f(y^{(n)} \mid \theta, h)) + \beta R(h)$$

where θ are the adjustable weighting coefficients of the DL network 170, h are the non-adjustable parameters (e.g., parameters selected by a user, such as the choice of reconstruction kernel), $y^{(n)}$ represents the nth input sinogram, $\bar{y}^{(n)}$ represents the nth target sinogram. The number N is the total number of training projections. In certain implementations, the following weighted mean absolute error loss function is used $$L(\bar{y}, y) = \sum_{j} d_j |y_j - \bar{y}_j|$$

wherein $d_j$ is the weight which has the form $$d_j = \bar{y}_j^p$$

with p being a scalar. The choice of this weight is inspired by the statistical mean estimation method where $d_j$ is often necessarily chosen to be the inverse of data noise variance. To handle the overfitting issue an additional regularization R on h is used, which is given by $R(h)=\Sigma_j h_j$. The regularization strength can be tuned thru the parameter β.

In certain implementations, the network 170 is trained using backpropagation. Backpropagation can be used for training neural networks and is used in conjunction with gradient descent optimization methods. During a forward pass, the algorithm computes the network's predictions based on the current parameters θ. These predictions are then input into the loss function, by which they are compared to the corresponding ground truth labels (i.e., the high-quality target data 153). During the backward pass, the model computes the gradient of the loss function with respect to the current parameters, after which the parameters are updated by taking a step of size of a predefined size in the direction of minimized loss (e.g., in accelerated methods, such that the Nesterov momentum method and various adaptive methods, the step size can be selected to more quickly converge to optimize the loss function).

The optimization method by which the backprojection is performed can use one or more of gradient descent, batch gradient descent, stochastic gradient descent, and mini-batch stochastic gradient descent. The forward and backwards passes can be performed incrementally through the respective layers of the network. In the forward pass, the execution starts by feeding the inputs through the first layer, thus creating the output activations for the subsequent layer. This process is repeated until the loss function at the last layer is reached. During the backward pass, the last layer computes the gradients with respect to its own learnable parameters (if any) and also with respect to its own input, which serves as the upstream derivatives for the previous layer. This process is repeated until the input layer is reached.

Returning to FIG. 5, step 317 of process 160 determines a change in the error as a function of the change in the network can be calculated (e.g., an error gradient), and this change in the error can be used to select a direction and step size for a subsequent change to the weights/coefficients of the DL network 170. Calculating the gradient of the error in this manner is consistent with certain implementations of a gradient descent optimization method. In certain other implementations, this step can be omitted and/or substituted with another step in accordance with another optimization algorithm (e.g., a non-gradient descent optimization algorithm like simulated annealing or a genetic algorithm), as would be understood by one of ordinary skill in the art.

In step 317 of process 160, a new set of coefficients are determined for the DL network 170. For example, the weights/coefficients can be updated using the changed calculated in step 317, as in a gradient descent optimization method or an over-relaxation acceleration method.

In step 318 of process 160, a new error value is calculated using the updated weights/coefficients of the DL network 170.

In step 319, predefined stopping criteria are used to determine whether the training of the network is complete. For example, the predefined stopping criteria can evaluate whether the new error and/or the total number of iterations performed exceed predefined values. For example, the stopping criteria can be satisfied if either the new error falls below a predefined threshold or if a maximum number of iterations is reached. When the stopping criteria is not satisfied the training process performed in process 160 will continue back to the start of the iterative loop by returning and repeating step 317 using the new weights and coefficients (the iterative loop includes steps 317, 318, and 319). When the stopping criteria are satisfied the training process performed in process 160 is completed.

Figure 6:
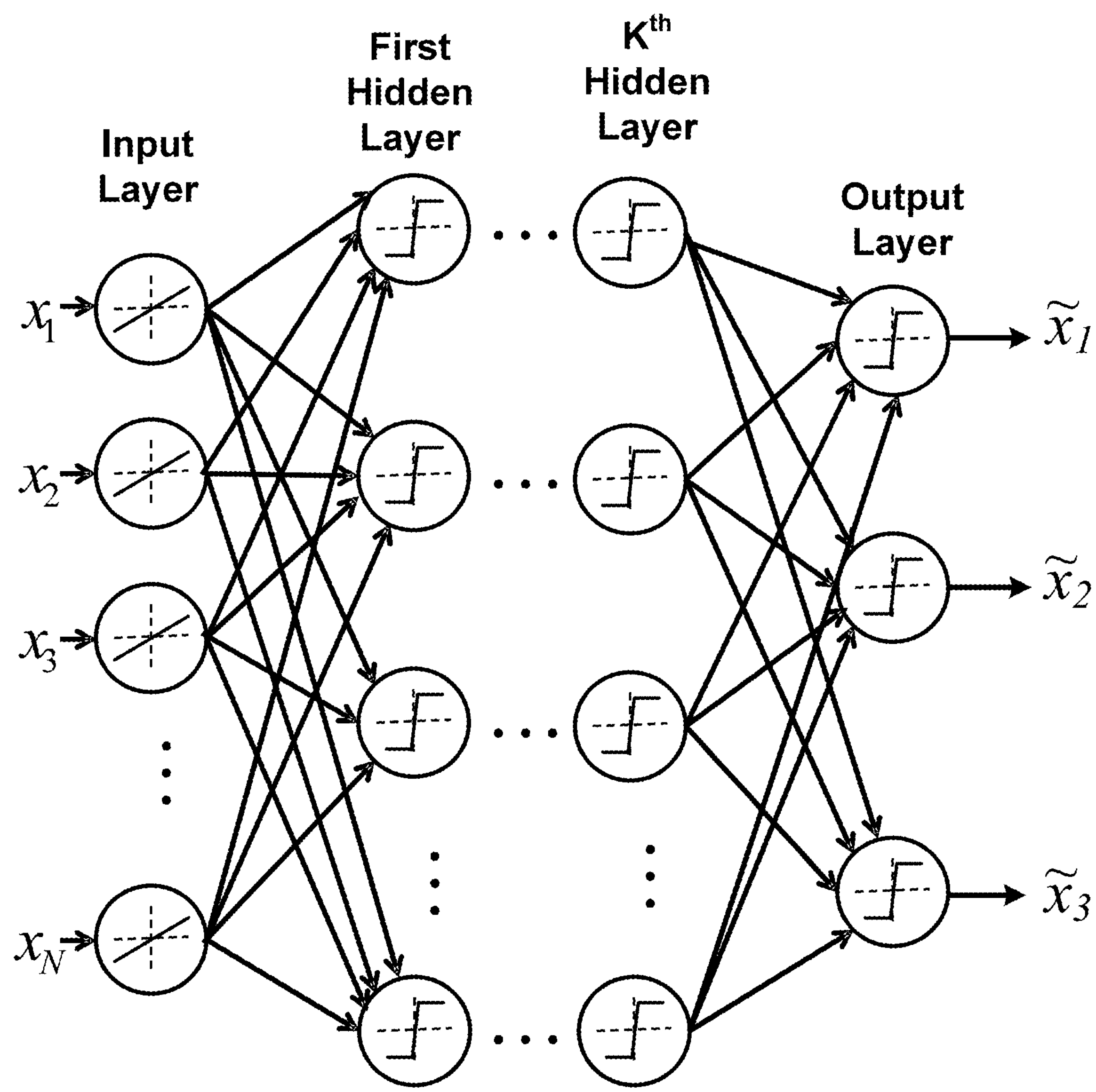
FIG. 6 shows an example of a DL network, according to one implementation.
Figure 7:
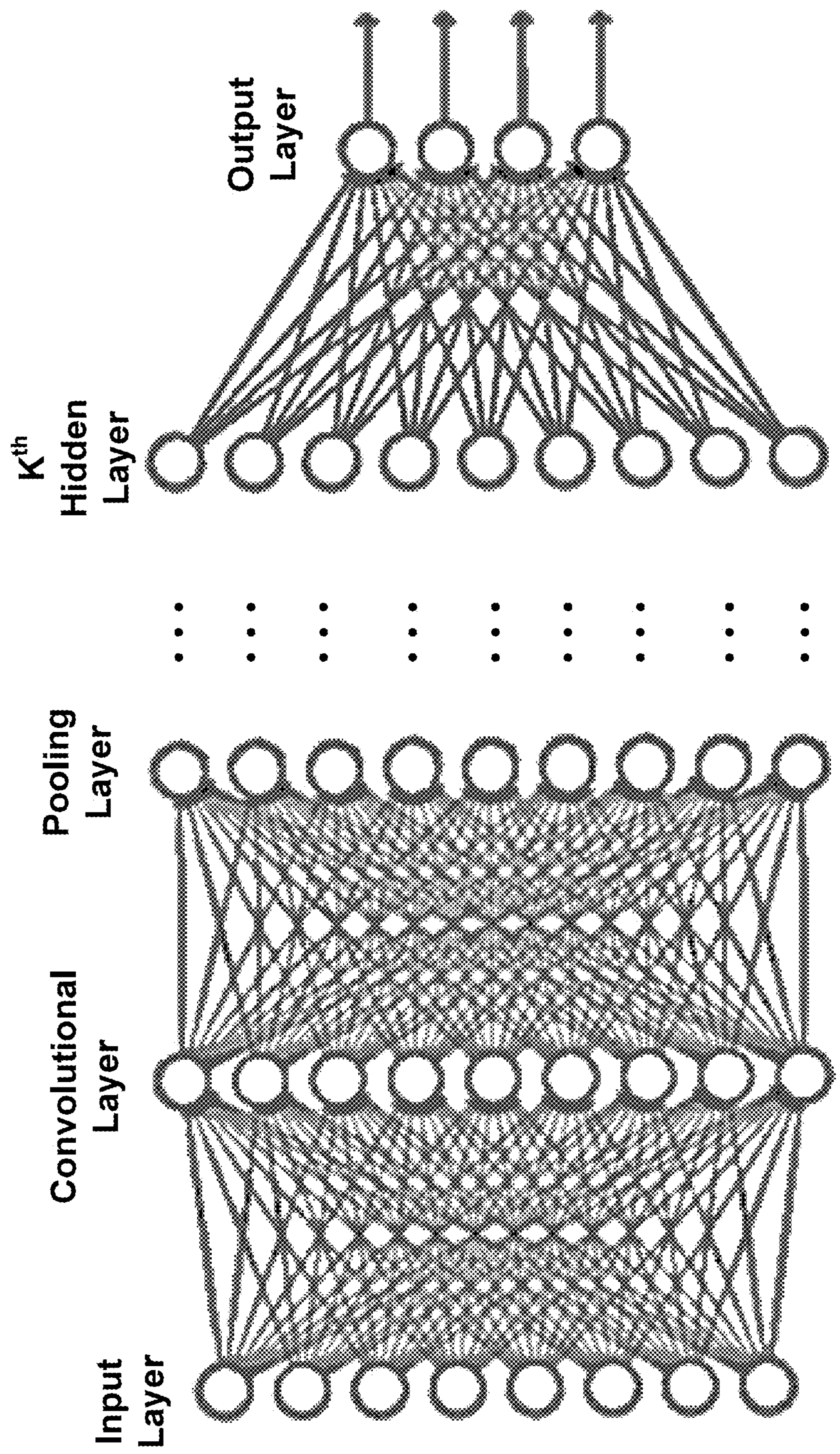
FIG. 7 shows an example of a type of DL network referred to as a convolutional neural network (CNN), according to one implementation.

FIGS. 6 and 7 show two examples of the inter-connections between layers in the DL network 170. The DL network 170 can include fully connected, convolutional, and the pooling layer, all of which are explained below. In certain preferred implementations of the DL network 170, convolutional layers are placed close to the input layer, whereas fully connected layers, which perform the high-level reasoning, are place further down the architecture towards the loss function. Pooling layers can be inserted after convolutions and proved a reduction lowering the spatial extent of the filters, and thus the amount of learnable parameters. Activation functions are also incorporated into various layers to introduce nonlinearity and enable the network to learn complex predictive relationships. The activation function can be a saturating activation functions (e.g., a sigmoid or hyperbolic tangent activation function) or rectified activation function (e.g., the Rectified Linear Unit (ReLU) applied in the first and second examples discussed above). The layers of the DL network 170 can also incorporate batch normalization, as also exemplified in the first and second examples discussed above.

FIG. 6 shows an example of a general artificial neural network (ANN) having N inputs, K hidden layers, and three outputs. Each layer is made up of nodes (also called neurons), and each node performs a weighted sum of the inputs and compares the result of the weighted sum to a threshold to generate an output. ANNs make up a class of functions for which the members of the class are obtained by varying thresholds, connection weights, or specifics of the architecture such as the number of nodes and/or their connectivity. The nodes in an ANN can be referred to as neurons (or as neuronal nodes), and the neurons can have inter-connections between the different layers of the ANN system. The synapses (i.e., the connections between neurons) store values called "weights" (also interchangeably referred to as "coefficients" or "weighting coefficients") that manipulate the data in the calculations. The outputs of the ANN depend on three types of parameters: (i) the interconnection pattern between the different layers of neurons, (ii) the learning process for updating the weights of the interconnections, and (iii) the activation function that converts a neuron's weighted input to its output activation.

Mathematically, a neuron's network function m(x) is defined as a composition of other functions $n_i(x)$, which can further be defined as a composition of other functions. This can be conveniently represented as a network structure, with arrows depicting the dependencies between variables, as shown in FIG. 6. For example, the ANN can use a nonlinear weighted sum, wherein $m(x)=K(\Sigma_i w_i n_i(x))$, where K (commonly referred to as the activation function) is some predefined function, such as the hyperbolic tangent.

In FIG. 6 (and similarly in FIG. 7), the neurons (i.e., nodes) are depicted by circles around a threshold function. For the non-limiting example shown in FIG. 6, the inputs are depicted as circles around a linear function, and the arrows indicate directed connections between neurons. In certain implementations, the DL network 170 is a feedforward network.

FIG. 7 shows a non-limiting example in which the DL network 170 is a convolutional neural network (CNN). CNNs are type of ANN that has beneficial properties for image processing, and, therefore, have specially relevancy for the applications of image denoising. CNNs use feed-forward ANNs in which the connectivity pattern between neurons can represent convolutions in image processing. For example, CNNs can be used for image-processing optimization by using multiple layers of small neuron collections which process portions of the input image, called receptive fields. The outputs of these collections can then tiled so that they overlap, to obtain a better representation of the original image. This processing pattern can be repeated over multiple layers having alternating convolution and pooling layers.

Following after a convolutional layer, a CNN can include local and/or global pooling layers, which combine the outputs of neuron clusters in the convolution layers. Additionally, in certain implementations, the CNN can also include various combinations of convolutional and fully connected layers, with pointwise nonlinearity applied at the end of or after each layer.

Figure 8:
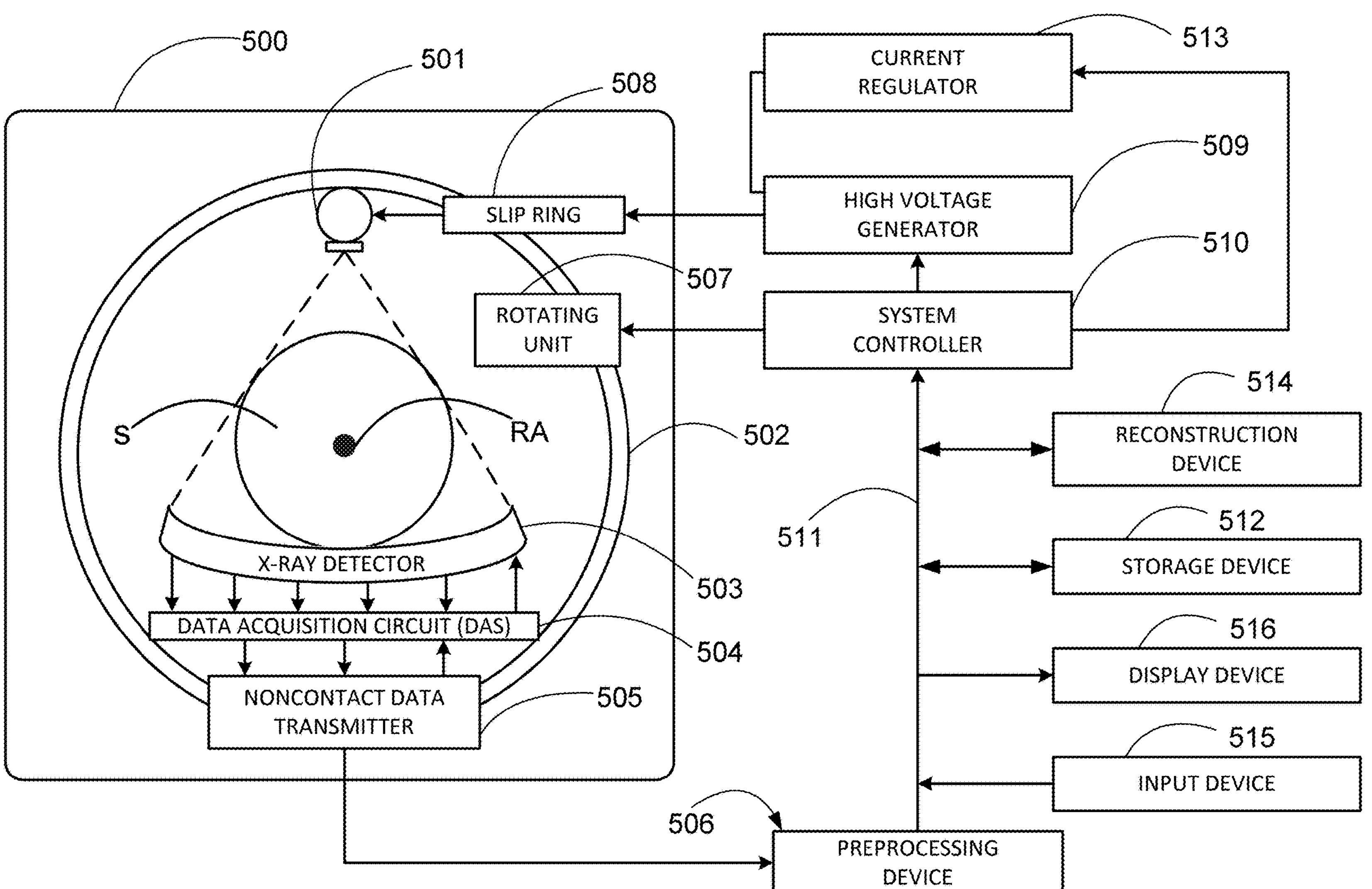
FIG. 8 shows a schematic diagram of an X-ray CT scanner, according to one implementation.

FIG. 8 illustrates a non-limiting example of a CT scanner. As shown in FIG. 8, a radiography gantry 500 is illustrated from a side view and further includes an X-ray tube 501, an annular frame 502, and a multi-row or two-dimensional-array-type X-ray detector 503. The X-ray tube 501 and X-ray detector 503 are diametrically mounted across an object OBJ on the annular frame 502, which is rotatably supported around a rotation axis RA.

The multi-slice X-ray CT apparatus further includes a high voltage generator 509 that generates a tube voltage applied to the X-ray tube 501 through a slip ring 508 so that the X-ray tube 501 generates X-rays. The X-rays are emitted towards the object OBJ, whose cross sectional area is represented by a circle. For example, the X-ray tube 501 having an average X-ray energy during a first scan that is less than an average X-ray energy during a second scan. Thus, two or more scans can be obtained corresponding to different X-ray energies. The X-ray detector 503 is located at an opposite side from the X-ray tube 501 across the object OBJ for detecting the emitted X-rays that have transmitted through the object OBJ. The X-ray detector 503 further includes individual detector elements or units.

The CT apparatus further includes other devices for processing the detected signals from X-ray detector 503. A data acquisition circuit or a Data Acquisition System (DAS) 504 converts a signal output from the X-ray detector 503 for each channel into a voltage signal, amplifies the signal, and further converts the signal into a digital signal.

The above-described data is sent to a preprocessing circuitry 506, which is housed in a console outside the radiography gantry 500 through a non-contact data transmitter 505. The preprocessing circuitry 506 performs certain corrections, such as sensitivity correction on the raw data. A storage 512 stores the resultant data, which is also called projection data at a stage immediately before reconstruction processing. The storage 512 is connected to a processing circuitry 510 through a data/control bus 511, together with a reconstruction device 514, input interface 515, and display 516. The processing circuitry 510 controls a current regulator 513 that limits the current to a level sufficient for driving the CT system.

The detectors are rotated and/or fixed with respect to the patient among various generations of the CT scanner systems. In one implementation, the X-ray tube 501 and the X-ray detector 503 are diametrically mounted on the annular frame 502 and are rotated around the object OBJ as the annular frame 502 is rotated about the rotation axis RA.

The storage 512 can store the measurement value representative of the irradiance of the X-rays at the X-ray detector unit 503. Further, the storage 512 can store a dedicated program for executing method 10.

The reconstruction circuitry 514 can execute various steps of method 10. Further, reconstruction circuitry 514 can execute pre-reconstruction processing image processing such as volume rendering processing and image difference processing as needed.

The pre-reconstruction processing of the projection data performed by the preprocessing circuitry 506 can include correcting for detector calibrations, detector nonlinearities, and polar effects, for example.

Post-reconstruction processing performed by the reconstruction circuitry 514 can include filtering and smoothing the image, volume rendering processing, and image difference processing as needed. The image reconstruction process can implement various steps of method 10. The reconstruction circuitry 514 can use the memory to store, e.g., projection data, reconstructed images, calibration data and parameters, and computer programs.

The various circuitry (e.g., the reconstruction circuitry 514 and preprocessing circuitry 506) can include a CPU (processing circuitry) that can be implemented as discrete logic gates, as an Application Specific Integrated Circuit (ASIC), a Field Programmable Gate Array (FPGA) or other Complex Programmable Logic Device (CPLD). An FPGA or CPLD implementation may be coded in VHDL, Verilog, or any other hardware description language and the code may be stored in an electronic memory directly within the FPGA or CPLD, or as a separate electronic memory. Further, the storage 512 can be non-volatile, such as ROM, EPROM, EEPROM or FLASH memory. The storage 512 can also be volatile, such as static or dynamic RAM, and a processor, such as a microcontroller or microprocessor, can be provided to manage the electronic memory as well as the interaction between the FPGA or CPLD and the memory.

In one implementation, the reconstructed images can be displayed on a display 516. The display 516 can be an LCD display, CRT display, plasma display, OLED, LED or any other display known in the art.

While certain implementations have been described, these implementations have been presented by way of example only, and are not intended to limit the teachings of this disclosure. Indeed, the novel methods, apparatuses and systems described herein may be embodied in a variety of other forms; furthermore, various omissions, substitutions and changes in the form of the methods, apparatuses and systems described herein may be made without departing from the spirit of this disclosure.

The invention claimed is:

1. An apparatus, comprising:

circuitry configured to obtain projection data representing an intensity of X-rays detected by a plurality of detectors, the X-rays being emitted from an X-ray source having a focal spot size that is larger than a predefined area threshold, acquire a neural network, the neural network having been trained using a training dataset including input data and target data, the input data including large-focal-spot-size X-ray projection data, the target data including small-focal-spot-size X-ray projection data, and the large-focal-spot-size X-ray projection data having a focal spot size greater than the predefined area threshold and the small-focal-spot-size X-ray projection data having a focal spot size less than the predefined area threshold; and apply the obtained projection data to the neural network to thereby output filtered projection data from the neural network.

2. The apparatus according to claim 1, wherein the circuitry is further configured to reconstruct a computed tomography (CT) image from the filtered projection data, wherein the obtained projection data is an acquired sinogram, the filtered projection data is a filtered sinogram, and the CT image has a higher resolution than would an image reconstructed from the obtained projection data.

3. The apparatus according to claim 1, wherein the circuitry is further configured to acquire the neural network, wherein the neural network has been trained using the target data that is acquired by averaging the X-rays detected by the plurality of detectors to obtain a signal to noise ratio greater than a signal to noise ratio of the input data, thereby training the neural network to denoise an input that is applied to the neural network.

4. The apparatus according to claim 1, wherein the circuitry is further configured to acquire the neural network, wherein the neural network has been trained with the training dataset in which the target data is acquired with a smaller point spread function than the input data, thereby the neural network is trained to increase a resolution of the filtered projection data relative to the obtained projection data.

5. The apparatus according to claim 1, wherein the circuitry is further configured to acquire the neural network, wherein the neural network is a residual network, and the filtered projection data are generated by subtracting an output of the network from the obtained projection data.

6. The apparatus according to claim 1, wherein the circuitry is further configured to train the neural network by obtaining the training dataset comprising input sinograms paired with respective target sinograms, using the neural network to generate output sinograms from the respective input sinograms by applying a given input sinogram to the neural network, thereby generating a corresponding output sinogram, and training the neural network by iteratively adjusting weighting coefficients of the neural network to minimize a value of a loss function, the loss function measuring a disagreement between the output sinogram and a target sinogram that corresponds to the output sinogram.

7. The apparatus according to claim 6, wherein the circuitry is further configured to train the neural network wherein the loss function includes a peak signal to noise ratio, a structural similarity index, and/or an $\ell_p$-norm of a difference between the respective target sinograms and the filtered sinograms corresponding to the input sinograms.

8. The apparatus according to claim 6, wherein the circuitry is further configured to train the neural network using the training dataset, wherein the input sinograms are acquired using a focal spot size greater than the predefined area threshold, and the target sinograms are acquired using a focal spot size less than the predefined area threshold.

9. The apparatus according to claim 1, wherein the circuitry is further configured to obtain the projection data, wherein the projection data is fluoroscopy data.

10. The apparatus according to claim 2, wherein the X-ray projection data is X-ray CT projection data, and the apparatus further comprises a rotatable gantry including the X-ray source configured on the gantry to rotate around an object, the X-ray source being an X-ray tube in which a size of a focal spot is controlled by an area of an electron beam on an anode and an angle of the anode with respect to a direction of an X-ray beam comprising the X-rays emitted from the anode, and a detector array including the plurality of detectors, the detector array being arranged on the gantry diametrically opposed to the X-ray source and configured rotate together with the X-ray source, the detector array being further configured to receive the X-rays emitted from the X-ray source at the plurality of detector elements to generate the projection data.

11. A method, comprising:

obtaining projection data representing an intensity of X-rays detected by a plurality of detectors, the X-rays being emitted from an X-ray source having a focal spot size that is larger than a predefined area threshold, acquiring a neural network, the neural network having been trained using a training dataset including input data and target data, the input data including large-focal-spot-size X-ray projection data, the target data including small-focal-spot-size X-ray projection data, and the large-focal-spot-size X-ray projection data having a focal spot size greater than the predefined area threshold and the small-focal-spot-size X-ray projection data having a focal spot size less than the predefined area threshold; and applying the obtained projection data to the neural network to thereby output filtered projection data from the neural network.

12. The method according to claim 11, further comprising reconstructing a computed tomography (CT) image from the filtered projection data, wherein the obtained projection data is an acquired sinogram, the filtered projection data is a filtered sinogram, and the CT image has a higher resolution than would an image reconstructed from the obtained projection data.

13. The method according to claim 11, wherein the step of acquiring the neural network further includes that the neural network has been trained using the target data that is acquired by averaging the X-rays detected by the plurality of detectors to obtain a signal to noise ratio greater than a signal to noise ratio of the input data, thereby training the neural network to denoise an input that is applied to the neural network.

14. The method according to claim 11, wherein the step of acquiring the neural network further includes that the neural network has been trained with the training dataset in which the target data is acquired with a smaller point spread function than the input data, thereby the neural network is trained to increase a resolution of the filtered projection data relative to the obtained projection data.

15. The method according to claim 11, wherein the step of acquiring the neural network further includes that the neural network is a residual network, and the filtered projection data are generated by subtracting an output of the network from the obtained projection data.

16. The method according to claim 11, further comprising train the neural network by obtaining the training dataset comprising input sinograms paired with respective target sinograms, using the neural network to generate output sinograms from the respective input sinograms by applying a given input sinogram to the neural network, thereby generating a corresponding output sinogram, and training the neural network by iteratively adjusting weighting coefficients of the neural network to minimize a value of a loss function, the loss function measuring a disagreement between the output sinogram and a target sinogram that corresponds to the output sinogram.

17. The method according to claim 16, wherein the step of training the neural network further includes that the loss function includes a peak signal to noise ratio, a structural similarity index, and/or an $\ell_p$-norm of a difference between the respective target sinograms and the filtered sinograms corresponding to the input sinograms.

18. The method according to claim 16, wherein the step of training the neural network further includes that the input sinograms are acquired using a focal spot size greater than the predefined area threshold, and the target sinograms are acquired using a focal spot size less than the predefined area threshold.

19. The method according to claim 11, wherein the step of obtaining the projection data further includes that the projection data is fluoroscopy data.

20. A non-transitory computer-readable storage medium including executable instructions, which when executed by circuitry, cause the circuitry to perform the method according to claim 11.

* * * * *